United States Patent [19]

Martin

[11] Patent Number: 4,756,708
[45] Date of Patent: Jul. 12, 1988

[54] BIOPSY CATHETER

[75] Inventor: Geoffrey S. Martin, Mississauga, Canada

[73] Assignee: Vas-Cath Incorporated, Mississauga, Canada

[21] Appl. No.: 56,830

[22] Filed: Jun. 2, 1987

Related U.S. Application Data

[63] Continuation-in-part of Ser. No. 701,255, Feb. 13, 1985, abandoned.

[30] Foreign Application Priority Data

Feb. 14, 1984 [CA] Canada .................... 447403

[51] Int. Cl.4 .................... A61M 11/00; A61B 5/00
[52] U.S. Cl. .................... 604/93; 128/768; 128/760; 604/280; 604/282; 604/283; 604/164; 604/170
[58] Field of Search ............ 604/93, 239, 240, 280, 604/281, 282, 283, 117, 158, 164, 170, 264; 128/740, 760, 767-768

[56] References Cited

U.S. PATENT DOCUMENTS

| | | | |
|---|---|---|---|
| 812,020 | 2/1906 | Crippen | 604/264 |
| 1,906,678 | 5/1933 | Wappler | 604/170 |
| 1,920,006 | 7/1933 | Dozier | 604/170 |
| 2,118,631 | 12/1938 | Wappler | 604/170 |
| 2,154,968 | 4/1939 | Alkio | 604/264 |
| 2,856,934 | 10/1958 | Petillo | 604/170 |
| 3,547,103 | 12/1970 | Cook | 604/170 |
| 3,766,907 | 10/1973 | Muenzer | 128/760 |
| 3,777,743 | 12/1973 | Binard | 128/760 |
| 4,405,314 | 9/1983 | Cope | 604/281 |
| 4,627,444 | 12/1986 | Brooker | 128/760 |
| 4,635,488 | 1/1987 | Kremer | 128/760 |

OTHER PUBLICATIONS

"Fetal Sex Prediction by Sex Chromatin of Chrorionic Villi Cells During Early Pregnancy", Chinese Medical Journal, vol. 1(2), pp. 117-126, Mar. 1975.

Primary Examiner—C. Fred Rosenbaum
Assistant Examiner—Gene B. Kartchner
Attorney, Agent, or Firm—Rogers & Scott

[57] ABSTRACT

A biopsy catheter for use in Chorionic Villi Sampling (CVS) has a flexible cannula and an obturator for stiffening the cannula during insertion. The cannula has a curved portion to facilitate insertion and the obturator has a very flexible leading portion connected to a straight portion. The leading portion of the obturator is in the form of a coiled spring wire which lies in the curved portion of the cannula during insertion and which is longer than this curved portion. The coiled spring wire has a very low resistance to bending about its longitudinal axis so that when the obturator is withdrawn the coiled spring wire flexes to follow the curve of the cannula with minimal resistance to avoid displacement of the cannula end after it is located for collecting a sample of villi.

6 Claims, 1 Drawing Sheet

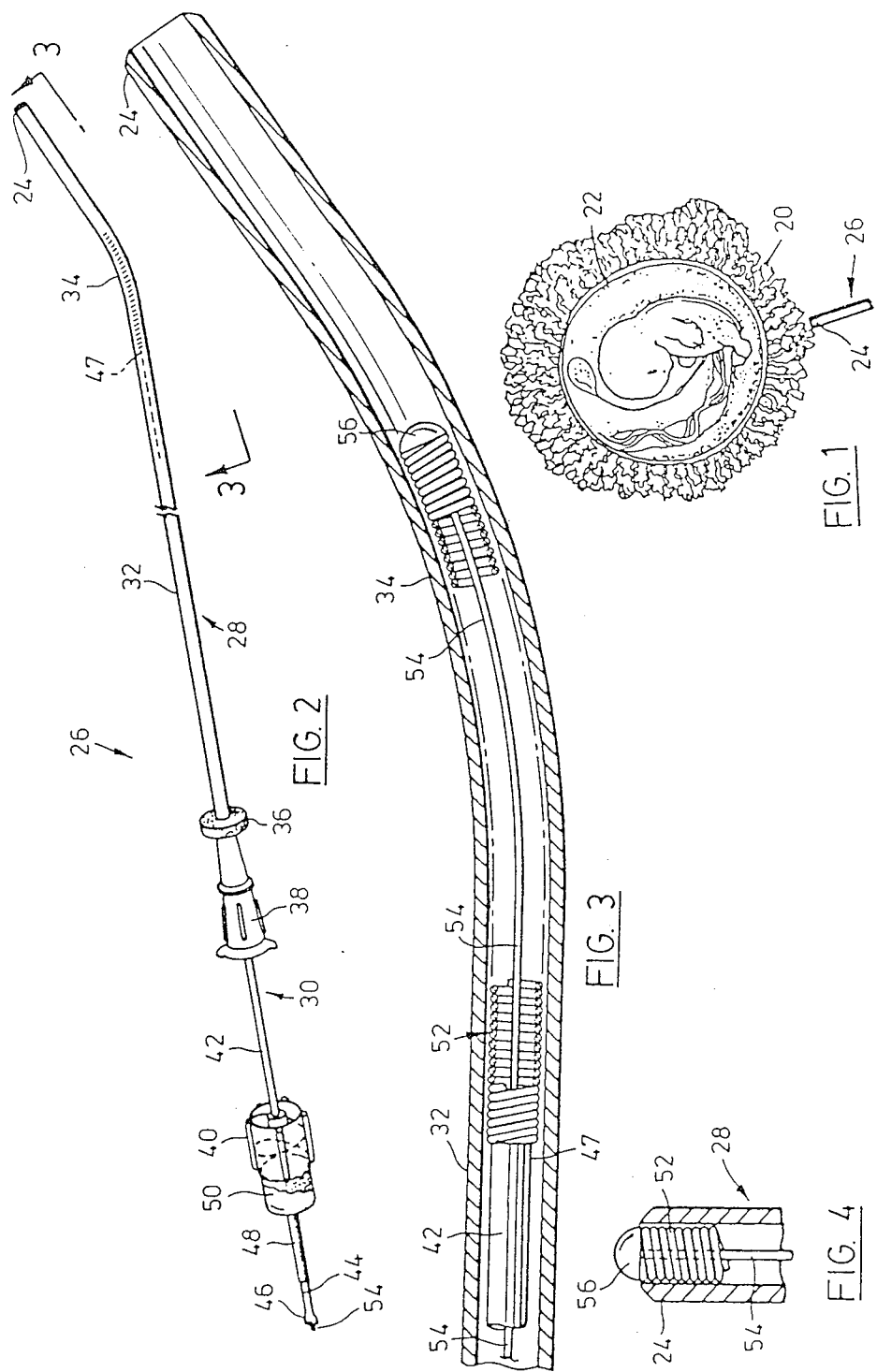

BIOPSY CATHETER

This is a continuation in-part of Ser. No. 701,255 filed Feb. 13, 1985, now abandoned and relates to biopsy catheters and particularly, but not exclusively, to catheters for taking biopsies from the chorionic membrane surrounding a seven to eight week old fetus, for subsequent analysis to determine the genetic health of the fetus.

During pregnancy, early detection of fetal defects is important, especially to older women, many of whom would rather have an abortion than give birth to a baby with a defect such as Downs Syndrome. In any procedure for the detection of early fetal defects it is important that the procedure should involve a minimal risk of miscarriage or of inadvertently inducing abortion. In addition, the test should be performed as soon as possible in the pregnancy, because a decision to abort the pregnancy becomes increasingly difficult, both emotionally and physically with the passage of time. The fetal detection test should also minimize the risk of inadvertently inducing abortion.

Since the 1960's, pregnant women (usually over 35) who have been concerned about the possibility of bearing a child with birth defects, relied on a test called amniocentesis to determine the presence of birth defects. This procedure involves the use of a syringe or large needle to withdraw a small amount of fluid surrounding the fetus from which assays can determine whether defective chromosomes are present. This procedure is typically performed after the fourth month of pregnancy. At this stage the growth of the fetus is so far advanced that a decision to abort can involve significant physical and emotional problems. Investigations of this procedure have produced statistics supporting the suggestion that the procedure causes miscarriages in one of every two hundred women tested. From such investigations it is evidently desirable to be able to detect the presence of fetal defects earlier in the pregnancy and also to reduce the risk of causing a miscarriage or inadvertent abortion. Another problem with amniocentesis is that it takes two to four weeks to grow recovered cells into sufficient quantity for study and consequently even with the earliest possible test a fetus has to be 18-20 weeks advanced before this test will yield accurate results.

A procedure presently undergoing clinical evaluation is Chorion Biopsy or Chorionic Villi Sampling (CVS). Chorionic villi are fingerlike projections of tissue in the chorionic membrane which eventually forms the placenta. Chorionic villi are well developed around the seventh to eighth week of pregnancy. The object of this procedure is to remove, by vacuum, a sample of the villi and assay the sample to determine the genetic health of the fetus. This procedure requires a physician to insert a thin catheter through the vagina and cervix into the uterus ending at the chorion membrane. When the catheter tip is located on the villi, a source of negative pressure is coupled to the catheter to withdraw a sample of villi tissue for analysis. The advantages of this procedure over the amniocentesis is that the biopsies or samples obtained provide enough tissue for analysis, which takes about ten days. Thus, early indications of fetal defects around the seventh to eighth week of pregnancy can be obtained.

To sample chorionic villi it is important that the catheter used is flexible to facilitate insertion yet is curved to conform to the anatomical configuration of the patient. Also, the catheter should have sufficient rigidity to be handled easily by the physician. In addition, once the catheter tip is located on the chorionic villi it is important that when the obturator is withdrawn the cannula tip remains in the selected location for removing villi from this location in sufficient quantity for analysis. Consequently the catheter must be sufficiently stiff to maintain its shape once it is positioned for use to withdraw villi.

One type of existing catheter is manufactured by Portex Limited (U.K.). The catheter comprises a hollow cannula and 1.5 mm diameter flexible aluminum obturator for inserting the cannula. In use, the physician inserts the obturator within the cannula and then bends the catheter to obtain the desired degree of bend for insertion. The catheter is then inserted to the desired location and finally the obturator is withdrawn. Although the aluminum obturator is flexible because it can be bent by hand, it retains sufficient rigidity in its bent position to straighten the curved portion of the cannula as it is removed thereby displacing the cannula tip from its originally desired location. Such displacement is a disadvantage because it may result in improper sampling and may necessitate further tests. Further, because the obturator retains some of its curvature it is difficult to cause it to pass through the outer end fitting on the cannula.

An object of the present invention is to provide an improved biopsy catheter especially for use in Chorionic Villi Sampling (CVS).

In one of its aspects the present invention provides an obturator for use with a cannula having a long straight portion blending into a shorter curved portion which may have different curvatures for different patients. In use the obturator is inserted into the cannula and the obturator has a straight portion and a more flexible leading portion which is longer than the curved portion of the cannula. During insertion and withdrawal of the obturator with respect to the cannula, the leading portion conforms to the cannula curve. Once the catheter is inserted so that the cannula tip is in its desired sampling location, the obturator is withdrawn and the leading portion flexes as it leaves the curved portion of the cannula without displacing the cannula tip from the selected sampling position because the curve in the cannula is unaffected.

In another of its aspects, the invention provides a catheter comprising a cannula having a long straight portion blending into a shorter curved portion, and the aforementioned obturator.

These and other aspects of the present invention will become apparent with reference to the following description and drawings in which:

FIG. 1 is a diagrammatic view of a fetus and shows a tip of a cannula next to the chorionic villi;

FIG. 2 is a perspective view of a preferred embodiment of a catheter with the obturator partially withdrawn; and FIG. 3 is a side view, partly sectioned, to a larger scale of part of the catheter taken on the line 3—3 in FIG. 2; and FIG. 4 is a view similar to FIG. 3 of an outer end of the catheter showing the obturator at the end of the cannula.

The purpose of the invention is to provide a catheter particularly for sampling villi during the early stages of pregnancy. FIG. 1 illustrates chorionic villi 20 of the chorionic membrane 22 and a forward end 24 of a preferred form of catheter 26 according to the invention in position to withdraw samples of the fingerlike villi. It is desirable to be able to position the end 24 using an obturator to occlude the opening in the end and then to remove the obturator while leaving the end in the same position. After such location, a vacuum is used of sufficient magnitude to draw part of the villi through the opening into the lumen of the cannula, which is then withdrawn and the sample removed for analysis.

The structure of catheter 26 is illustrated in FIG. 2 and shows a cannula 28 with an obturator 30 partially withdrawn. The cannula typically has an outside diameter of 0.065 inches and has a long relatively straight portion 32 about 6 inches long and which extends forwardly and integrally into a shorter curved portion 34 with a length of about 2.13 inches. The curved portion facilitates insertion of the catheter and terminates at the forward end 24 defining the end opening which has an internal diameter of about 0.042 inches. The cannula is formed of material which is flexible while having sufficient rigidity to maintain its curved shape.

A rubber disc 36 is mounted over the straight portion 32 of the catheter to facilitate handling of the cannula and to set the depth of penetration of the catheter. A male luer fitting is attached to the outer end of the cannula for connection to a female luer fitting 40 on the obturator 30 for insertion and to a tube from a vacuum source for sampling.

The obturator 30 has a straight portion 42 of stainless steel. This portion is relatively long and preferably tubular. The portion passes through the female luer fitting 40 and has a forward end portion 44 with a flattened end 46 projecting beyond the end of the fitting 40. The end portion is covered by a 3/32 inches diameter tube 48 of heat shrunk polyolefin and is shown partly cut-away in the interest of clarity. The tubular portion 42 is slidably mounted in a solid cylindrical rubber plug 50 fixed to the fitting 40 so that the portion 42 can be held by the projecting end portion 44 and pushed or pulled relative to the luer fitting 40. Friction between the plug 50 and the portion 42 holds these parts in their relative positions until disturbed by finger forces. The tubular portion 42 extends to end at 47 where it meets a leading portion 52 which is made of tightly wound coils of very light spring wire as will be described with reference to FIG. 4.

The leading portion 52 is about 2.28 inches long, i.e. slightly longer than the length of the curved portion 34. The coil spring wire is about 0.007 inches diameter and is wound into tight coils of about 0.038 inches diameter. The coils have a very low resistance to flexing so that this portion is readily displaced relative to the longitudinal axis of the leading portion 52. As a result the portion places a negligible deflecting force on the curved portion 34 of the cannula when it is inserted inside this curved portion.

The wire forming the coils of portion 52 has a part 54 led back inside the coils, through the tubular portion 42 ending clamped inside the flattened end 46. Thus, the coils are held in tight arrangement by this part of the wire with the one end of the coils in engagement with the adjacent end of the straight portion of the obturator.

The exposed end of the leading portion 52 is covered by a rounded weld 56 to remove rough edges.

The lengths of the portions 32, 34 of the obturator are chosen so that when the portion 32 is manipulated relative to the rubber plug 50 prior to insertion, the rounded portion 56 is positioned just beyond the end 24 of the cannula 28 as shown in FIG. 5 it presents with the rounded end 24 a smooth surface for insertion.

To perform a Chorionic Villi Sampling test (CVS) the physician ensures that the rounded end 56 of the obturator is positioned as shown in FIG. 4 by moving the outer end portion 44 relative to the plug 50. Then, using ultrasonic guiding apparatus to which the obturator is sonar opaque, the physician inserts the catheter through the cervix into the uterus of the patient and locates the end 24 of the catheter next to the chorionic villi 20 as shown in FIG. 1. Once the physician is satisfied that the catheter is in the correct position for sampling he then rotates the luer fitting 40 to permit the obturator to be withdrawn. During withdrawal of the obturator, the leading portion 52 flexes readily to follow the shape of the curved portion 34 so that there is no displacement of the end 24 of the flexible cannula from its originally located position. When the obturator 30 is withdrawn completely the physician then connects a vacuum tube or syringe to the luer fitting 38 and operates a vacuum pump to obtain a sample of chorionic villi. Once the physician is satisfied that a satisfactory biopsy has been taken he will then withdraw the cannula.

The biopsy can be assayed within ten days to provide rapid results. In the event that the test is improperly performed the testing procedure is so straightforward that it can be repeated with minimal work or discomfort to the patient.

Advantages of the present invention are that it permits fetal defects to be assessed at a much earlier stage in the fetal development. Use of the catheter carries minimal risk of causing miscarriage or inadvertent abortion and the curved catheter permits the catheter end to be located within a specific circumference simply by rotating it. Also, the catheter provides a sufficiently large tissue sample to facilitate immediate analysis and provide an accurate indication of fetal defects.

It will also be noted that the novel obturator permits the physician to withdraw the obturator with confidence that the tip will not be displaced from the intended sampling position during withdrawal thus facilitating more accurate results with less chance of repeat tests being needed.

The structure and materials used can be modified within the scope of the invention described with reference to the preferred embodiment, and such modifications are within the scope of the invention as claimed.

I claim:

1. A catheter for chorionic villi sampling, the catheter comprising:

a flexible cannula having a relatively long and substantially straight portion and a shorter curved portion blending into and extending forwardly from a forward end of the straight portion, the curved portion ending at a forward end of the cannula and defining an opening and, at the other end of the cannula, the straight portion including connector means; and an obturator for insertion into the cannula at said other end and having a rounded end for occluding the opening in the forward end of the cannula, the obturator having a very flexible portion extending from the rounded end and being longer than said curved portion and a stiffer portion extending from the flexible portion along a substantial length of the straight portion for terminating outside the cannula when the obturator is in position in the cannula with the rounded end at said opening whereby in use the cannula with the obturator is first positioned with the opening adjacent villi, the obturator is then withdrawn leaving the forward end of the cannula substantially undisturbed, and villi are drawn through the cannula by use of negative pressure.

2. A catheter as claimed in claim 1 wherein the flexible portion of the obturator consists of tightly wound coils of spring wire.

3. A catheter as claimed in claim 2 wherein the obturator has a wire extending through the leading and straight portions, the wire being secured to said tip and to the straight portion.

4. A catheter as claimed in claim 3 wherein the straight portion of the obturator is a stainless steel tube having a flattened end remote from the flexible portion to secure the core wire to the straight portion.

5. A catheter as claimed in claim 1 wherein the straight portion of the obturator is a friction fit in said connector means and the straight portion projects proximally out of the end of the connector means, so that the obturator can be moved to locate the tip relative to the cannula.

6. A catheter as claimed in claim 1 wherein the tip of the leading end of the cannula is rounded to facilitate insertion.

* * * * *